United States Patent [19]

Kollar

[11] 4,412,084
[45] Oct. 25, 1983

[54] PROCESS FOR PRODUCING ETHYLENE GLYCOL

[76] Inventor: John Kollar, 6 Spencer Ct., Wyckoff, N.J. 07481

[21] Appl. No.: 352,919

[22] Filed: Feb. 26, 1982

Related U.S. Application Data

[63] Continuation-in-part of Ser. No. 286,721, Jul. 28, 1981, abandoned, which is a continuation-in-part of Ser. No. 183,537, Sep. 2, 1980, Pat. No. 4,337,371.

[51] Int. Cl.$^3$ .................... C07C 31/20; C07C 29/00
[52] U.S. Cl. .................................................. 568/852
[58] Field of Search ...................................... 568/852

[56] References Cited

U.S. PATENT DOCUMENTS 4,345,104  8/1982  Cropley .............................. 568/852

FOREIGN PATENT DOCUMENTS 2844637  1/1980  Fed. Rep. of Germany ...... 568/860
1040735  9/1966  United Kingdom ................ 562/470

OTHER PUBLICATIONS

Oyama, "J. Org. Chem.", 30, Jul. 1965, pp. 2429-2432.
Vogel, "Practical Organic Chemistry", 3rd Ed. 1957, pp. 358, 359, 389, 414, 432, 463.

*Primary Examiner*—J. E. Evans

[57] ABSTRACT

In the preparation of ethylene glycol by reacting methanol, formaldehyde and an organic peroxide, improved yields of ethylene glycol are achieved by the reaction of portions of the total amounts of formaldehyde and peroxide to be reacted with methanol. Formaldehyde and peroxide are incrementally added to a liquid medium containing methanol in controlled amounts during the reaction to permit conversion of each portion of said formaldehyde and peroxide reactants prior to the next addition. The portions are added such that the concentration of glycol in the reaction medium to which a later portion is added is greater than that to which an earlier portion is added. The reaction is continued until all the formaldehyde and peroxide has been incrementally added to the reaction medium and subjected to reaction conditions for a suitable period of time.

14 Claims, No Drawings

PROCESS FOR PRODUCING ETHYLENE GLYCOL

This application is a continuation-in-part application of U.S. Ser. No. 286,721 filed July 28, 1981 entitled "Improved Process for Producing Ethylene Glycol", now abandoned, which in turn is a continuation-in-part application of U.S. Ser. No. 183,537 filed Sept. 2, 1980 entitled "Production of Ethylene Glycol by Reaction of Methanol, an Organic Peroxide and Formaldehyde", now U.S. Pat. No. 4,337,371, the disclosure which is incorporated herein by reference.

This invention relates to a process for producing ethylene glycol from methanol.

BACKGROUND OF THE INVENTION

Dwindling petroleum reserves and increasing prices have placed an increased emphasis on the use of synthesis gas in place of oil as a starting material for various chemicals such as methanol, formaldehyde and ethylene glycol. The advantage of synthesis gas is that it can be produced from raw materials other than petroleum such as natural gas or coal, and potentially from oil shale and tar sands.

An example of an industrial process for the production of ethylene glycol utilizing synthesis gas as a starting material is the reaction of formaldehyde with carbon monoxide and water at high pressures (over 300 atmospheres) in the presence of an acid catalyst to produce hydroxyacetic (glycolic) acid which is then reacted with methanol to give the methyl ester; the latter is then converted to the glycol by catalytic hydrogenation. See U.S. Pat. Nos. 2,316,564 issued Apr. 13, 1943 to Cockerill; 2,153,064 issued Apr. 4, 1939 to Larson; and 2,152,852; 2,385,448 and 2,331,094 issued Apr. 4, 1939, June 9, 1942 and Oct. 5, 1943, respectively, to Loder.

Another proposed process utilizing synthesis gas for the production of ethylene glycol is the reaction of methanol and carbon monoxide using a rhodium-catalyzed, high pressure process; see U.S. Pat. Nos. 4,115,428 issued to Vidal et al and 4,115,433 issued to Cosby et al on Sept. 19, 1978.

With respect to the type of process for the production of ethylene glycol disclosed and claimed herein, it should be noted that the oxidative dimerization or dehydrodimerization of a large variety of organic compounds by peroxides is very old art that was pioneered by the preeminent free radical theoretician M. S. Kharasch and his students. These studies became the foundations of much subsequent free radical chemistry. Karasch et al in JACS 65, 15, 1943 shows the dehydrodimerization of acetic acid to succinic acid with acetyl peroxide in a 50 mole percent utilization selectivity based on acetyl peroxide, utilization selectivity being defined as the moles of dehydrodimer product made divided by the moles of peroxide converted. Isobutyric acid produced tetramethyl succinic acid in a 42.4 mole percent utilization selectivity. Kharasch et al in J. Org. Chem. 10, 386, 1945 show the ester methyl chloroacetate being dimerized to dimethyl dichloro succinate by acetyl peroxide in a 41 percent utilization selectivity. Kharasch et al in J. Org. Chem. 10, 401, 1945 show the dimerization of cumene and ethyl benezene with acetyl peroxide in 61.9 mole percent and 32.1 mole percent respectively to their dehydrodimers. Wiles et al in I, E & C, August 1949, page 1682, tell of the efficacy of di-t-butyl peroxide and 2,2 bis (t-butyl peroxy) butane for the dimerization of cumene. The benzoate ester of benzyl alcohol was dimerized to the dibenzoate ester of the corresponding glycol, diphenylene glycol, with di-t-butyl peroxide by Rust et al JACS 70, 3258 (1948).

The literature is replete with many other examples that produced the dehydrodimers at very low concentrations at utilization selectivities of generally from 20–50 mole percent based on the peroxide consumed. These selectivities are generally too low for the process to be considered for commercial development.

In connection with ethylene glycol, two teachings involving peroxide-induced reactions should be mentioned.

The first is described by Schwetlick et al, *Angew. Chem.* 72, 1960, No. 21, pages 779 and 780, and involves heating a mixture of di-tertiary butyl peroxide and methanol in a molar ratio of 1:20 in an autoclave and/or under reflux for a period of 10 hours at 140° C. A 26 percent yield of ethylene glycol is reported, with the statement being made that an increase in the alcohol excess raises the yields.

The second and more important of such other reaction paths to ethylene glycol, in terms of its relevance to the present invention, is described by Oyama in *J. Org. Chem.* 30, July, 1965, pages 2429–2432. In particular Oyama shows the reaction of 9 moles of methanol, 1.8 moles of 15 percent aqueous formaldehyde and 0.45 moles of t-butyl peroxide (di-tertiary butyl peroxide) at 140° C. for 12 hours to give 0.21 moles of ethylene glycol (Table I at the top of the right hand column on page 2430), with the statement being made immediately below Table I: "The yield of ethylene glycol in the reaction of formaldehyde with methanol is higher than that of t-butyl peroxide induced dimerization of methanol. This fact suggests that hydroxymethyl radical (D) adds to formaldehyde." Oyama describes in greater detail how this reaction was run and the products obtained, and contrasts it with the dehydrodimerization of methanol in the presence of t-butyl peroxide and the absence of formaldehyde, in the "Experimental" section beginning at page 2431 (particularly the sections headed "Reaction of Methanol with Formaldehyde" and "Dimerization of Methanol" on page 2432).

The yields of ethylene glycol obtained by Oyama are fairly low. Oyama's only run with methanol—that involving the above-described reaction of methanol, aqueous formaldehyde and t-butyl peroxide at 140° C. for 12 hours—gave only 1.86 weight percent of ethylene glycol.

The above-described reaction can be made to produce higher yields of ethylene glycol by substantially decreasing the amount of organic peroxide employed, relative to the amounts of formaldehyde and methanol present, from that employed by Oyama. Moreover, increasing the amount of methanol and decreasing the amount of water, relative to the other components of the reaction mixture, in contrast to the amounts employed by Oyama, also appear to contribute to the production of higher yields of ethylene glycol. Thus, for example, heating a mixture of 78.5 weight percent of methanol, 1.5 weight percent of di-tertiary butyl peroxide, 6.9 weight percent of formaldehyde and 13.1 weight percent of water at 155° C. for 2 hours gave a yield of 4.5 weight percent of ethylene glycol in the product mixture. This is equivalent to a yield of about 7.1 moles of ethylene glycol per mole of di-tertiary-butyl peroxide employed. (Oyama obtained 0.466 mole of ethylene glycol per mole of di-tertiary-butyl peroxide in his reaction). This improvement is more fully disclosed in the copending parent of this application, U.S. Ser. No. 183,537, filed Sept. 2, 1980.

THE INVENTION

In accordance with the process of this invention, improved yields of ethylene glycol can be achieved by the reaction with methanol of portions in sequence of the total amounts of formaldehyde and peroxide added to a liquid medium containing the methanol. Portions of the formaldehyde and peroxide are incrementally added to the liquid reaction medium during the reaction to permit at least a fraction of the final conversion of the reactants of formaldehyde, peroxide and methanol to take place prior to the addition of the next added portion of formaldehyde and peroxide. The next added portion of formaldehyde and peroxide is added to a zone of the methanol reaction medium wherein the fraction of the final conversion of the reactants has taken place with the concentration of glycol in the reaction medium to which a later portion is added being greater than that to which an earlier portion is added. The incremental additions of formaldehyde and peroxide are added until the entire amounts of the reactants utilized in the process have been added to the reaction zone and subjected to reaction conditions. In the process of this invention, higher amounts of ethylene glycol are produced when the formaldehyde and peroxide reactants are added incrementally to methanol compared to the amounts of ethylene glycol produced in the process when the entire amounts of the reactants utilized in the process are initially present in the reaction medium.

It is desirable to react formaldehyde, peroxide and methanol in the presence of a minor amount of basic material which serves to reduce the hydrogen ions that are being formed in the reaction in the form of acids without interferring with ethylene glycol content. Since these acids in the reaction catalyze the formation of undesirable by-products such as methylal, the basic material by neutralizing all or part of the acid has the effect of significantly reducing the amount of by-product formed.

In the present invention, the basic material can be present in the liquid reaction medium at the start of the reaction or can be incrementally added to the reaction medium with formaldehyde and peroxide. The amount of basic material used should be sufficient to neutralize or partially neutralize the acid being formed to prevent the acid catalyzed reaction of methanol and formaldehyde to methylal. If too much basic material is added to the reactants, the formaldehyde present may be converted to formose sugars which will be readily apparent by the amber color of the reactants, characteristic odor of the reaction liquid and the low formaldehyde accountability of the process. Also too much basic material may inhibit the production of ethylene glycol.

The term "portions" as used herein denotes fractions of the total amount of formaldehyde, peroxide, and in some instances basic material which will be added to the liquid reaction medium containing methanol during the reaction. For example, the amounts of these reactants can be divided into two portions wherein one portion is added at the beginning of the reaction and the remaining portion added later to complete the reaction. This would be a two stage addition reaction. The terms "multiple stage addition" or "incremental addition" are defined as the addition of portions of formaldehyde, peroxide and in some instances basic material in the form of two or more stages to as high as 10 stages or higher if desired, and in some instances can include a steady state addition of these portions of reactants in small amounts over the time of the reaction period. The phrase "a degree of conversions of the incrementally added portions of formaldehyde and peroxide" is defined as the reaction of formaldehyde and peroxide with methanol to form other products.

The term "basic material" as used in this specification and claims is meant to include those materials which are alkaline and will control the amount of hydrogen ions being produced in the form of acids in the reaction. Suitable basic materials include the hydroxides of alkali metals including lithium, sodium, potassium, rubidium, or cesium or alkaline earth metals such as calcium, strontium, barium, beryllium or magnesium. Also included in the term "basic material" are the salts of an alkali or alkaline earth metal and a weakly ionized acid such as oxalic, tartaric, malic, citric, formic, lactic, acetic, carbonic, phosphoric, pyrophosphoric, pyrophosphorous, propanoic, butyric, and others known in the art. Of specific interest for purposes of this invention, are the sodium and potassium salts of weakly ionized acids such as acetic, formic, oxalic, carbonic (including bicarbonates) or phosphoric. Examples of these sodium and potassium salts are sodium acetate, potassium acetate, sodium bicarbonate, potassium bicarbonate, sodium formate, potassium formate, sodium oxalate, potassium oxalate, sodium carbonate, potassium carbonate, sodium pyrophosphate, potassium pyrophosphate, sodium phosphate, potassium phosphate, sodium diphosphate, potassium diphosphate and the like. The amount of sodium or potassium salt or a weakly ionized acid added to the reactants can range from about 50 to about 3500 parts per million, preferably about 100 to about 3000 parts per million and more preferably about 100 to about 1500 parts per million of the initial reaction mixture. In the case of other basic materials, the amount should be equivalent to the amount stated for sodium and potassium salts of weakly ionized acids with regard to their ability to neutralize hydrogen ions in the system at hand. It a metal hydroxide such as sodium hydroxide or potassium hydroxide is utilized as the basic material, the amount added should be no greater than would be required to neutralize the acids being formed in the reaction. For example if sodium hydroxide is used as the basic material, about 25 to about 60 parts per million of the total reaction product results in reduced amounts of methylal compared to the reaction containing no basic material without undue sacrifice of the amount of ethylene glycol produced. In addition to those described previously, basic materials which can be used are zinc oxide, basic alumina, various basic thorium compounds and in general any basic material which will reduce the hydrogen ions of the acids produced without unduly reducing the ethylene glycol production due to by-product formation.

In general, reaction mixtures employed in practicing the present invention will contain from about 0.25 to about 25 weight percent, preferably no higher than about 6 weight percent, more preferably about 0.75 to 3 weight percent of organic peroxide. In most cases, the reaction mixture will also contain from about 45 to about 97 weight percent, preferably from about 80 to about 85 weight percent of methanol, and from about 0.5 to about 13 weight percent, preferably from about 2 to about 12 weight percent of formaldehyde, and from about 0.5 to about 35 weight percent, preferably from about 2 to about 10 weight percent of water.

The reaction will generally be carried out at a temperature of from about 100° C. to about 200° C., preferably from about 125° C. to about 175° C.

In the overall reaction of formaldehyde, peroxide and methanol to ethylene glycol, complete conversions of the incrementally added reactants of formaldehyde and peroxide are not necessary prior to addition of the next portion of reactants. However, the reaction should be carried out for a sufficient time to permit a substantial degree of conversion in each stage, i.e., upon addition of a portion of reactants and prior to addition of the next portion, or in the case of the final stage, prior to withdrawal and purification of the product stream. In general, the reaction will be allowed to proceed for an overall reaction time of from about 5 minutes to about 15 hours, preferably, from about 30 minutes to about 6 hours. The amount of time that the reaction is allowed to proceed in each stage will generally be equal to the overall reaction time divided by the number of stages. Thus, the range of time of reaction in each stage will be the range of the overall reaction time as given above divided by the number of stages. Generally, the higher the temperature, the lower the reaction time necessary to bring the reaction to a desired state of completion. There is little or no criticality in the pressure at which the reaction is carried out. Pressures of between autogenous pressure (in a closed reactor) to about 600 psig can be utilized.

The organic peroxide employed in the process of this invention has the formula $$R-O-O-R^1$$

wherein R and $R^1$ is each an alkyl or aralkyl group having 3 to 12 carbon atoms. Organic peroxides which may be employed are, for example di-tertiary-butyl peroxide, di-cumyl peroxide, tertiary-butyl-cumyl peroxide and tertiary-butyl ethylbenzyl peroxide. The preferred organic peroxide is di-tertiary-butyl peroxide.

An inert solvent may be employed in the process, although in most cases it is preferred to operate without one. Any solvent which does not react under conditions of the process may be employed, e.g. benzene and tertiary-butyl alcohol. When a solvent is employed, it will generally be in an amount up to about 25 percent by weight of the total reaction medium, although larger amounts can be used in some instances.

The reactions may be carried out batchwise wherein a reactor such as a stirred autoclave is charged with the initial reaction mixture and portions of the formaldehyde and peroxide and in some cases basic material, are sequentially and incrementally added to the methanol reaction medium. After all of the portions of reactants are added, the reaction is continued until the desired degree of reaction has taken place, after which the product mixture is withdrawn and purified. Another technique is a semi-continuous method in which the initial reaction mixture and incremental additions of reactants are charged to the methanol reaction medium, reaction takes place, and the product mixture periodically withdrawn from the reactor and purified.

A continuous reaction can be carried out in a reactor constructed so that under the conditions of reaction, a glycol concentration gradient occurs between the point where the first portions of peroxide and formaldehyde are added and that at which the glycol-containing product is withdrawn. In accordance with this invention, subsequent portions of peroxide and formaldehyde are added between these two points. For example, a continuous process may be carried out by causing the liquid reaction medium to flow through a pipe and adding portions of the formaldehyde and peroxide reactants at intervals along the pipe, forming a moving reaction medium containing a concentration gradient of glycol as it travels through the pipe. Thus, the additional individual portions of the reactants are added in a controlled manner along the pipe to the moving reaction medium until all the portions of reactants have been added. At the end of the pipe or reactor, the reaction of each portion of the reactants in the reaction medium has occurred at a conversion level to provide a product stream containing the desired amount of ethylene glycol. Alternatively, a baffled reactor may be employed containing a liquid reaction medium with a glycol concentration gradient between the point of entry of the initial feed stream and the point of exit of the product stream, wherein additional portions of peroxide and formaldehyde are added between the two points. In each case, the product mixture may then be purified using conventional techniques such as distillation or solvent extraction to obtain ethylene glycol in the desired purity, preferably fiber grade, and by-products such as tertiary-butyl alcohol, methylal, methyl formate, glycerine and acetone.

The following examples will illustrate the invention.

EXAMPLES 1-6

These examples show a direct comparison of the use of equivalent total amounts of reactants used in a single stage reaction vs. a multiple stage reaction to produce ethylene glycol (EG) by the reaction of formaldehyde ($CH_2O$) containing water ($H_2O$), di-tertiary-butyl peroxide (DtBP) and methanol (MeOH) in the presence of sodium bicarbonate ($NaHCO_3$). The formaldehyde used in these examples contained 4.54 parts per million sodium hydroxide per one weight percent formaldehyde used. The reactor was a 316 stainless steel 1" diameter pipe having a capacity of approximately 85 millimeters liquid. In a one stage reaction, all the reacting ingredients were placed in the reactor which was sealed and heated to 155° C. for 1 hour at autogenous pressure. In a staged reaction, a portion of the reactants of di-tertiary-butyl peroxide, formaldehyde and water and sodium bicarbonate were initially added to the reactor containing all the methanol heated to 155° C. for one hour. After the first hour of reaction, additional portions of the reactants were added and the reaction was conducted for another hour. After the second hour, the remainder of the reactants were added to the reactor and the reaction conducted for the final hour. After the reaction was completed in the first stage or in each multiple stage reaction, the reactor was cooled by quenching, vented, discharged and the contents analyzed by gas chromatography for ethylene glycol (EG) and other products.

The results of these examples are shown in Table I which sets out the total amounts of peroxide, formaldehyde and water charged to the reactor containing the methanol in the various stages. The amounts of reactants used are reported as weight percent of the total material in the reactor up to that stage. The amounts of ethylene glycol are reported as weight percent of the total product mixture.

TABLE I

COMPARISON OF ONE STAGE VS. THREE STAGE REACTION

| Example | Type of Reaction | | Reactants Added | | | NaHCO₃ Parts Per Million | Reaction Temp °C. | Reaction Time, Hrs. | Ethylene Glycol Wt % |
|---|---|---|---|---|---|---|---|---|---|
| | | | DtBP Wt % | H₂CO Wt % | H₂O Wt % | | | | |
| 1 | 1 stage | | 7.0 | 14.0 | 1.91 | 100 | 155 | 1 | 8.75 |
| 2 | 3 stage | 1st stage | 3.0 | 6.0 | .8 | 50 | 155 | 1 | 6.14 |
| | | 2nd stage (total) | 5.0 | 10.0 | 1.36 | 75 | 155 | 1 + 1 = 2 | 9.28 |
| | | 3rd stage (total) | 7.0 | 14.0 | 1.91 | 100 | 155 | 2 + 1 = 3 | 11.68 |
| 3 | 1 stage | | 5.0 | 13.0 | 1.77 | 100 | 155 | 1 | 8.01 |
| 4 | 3 stage | 1st stage | 2.0 | 6.0 | 0.80 | 50 | 155 | 1 | 4.81 |
| | | 2nd stage (total) | 3.5 | 9.5 | 1.30 | 75 | 155 | 1 + 1 = 2 | 8.16 |
| | | 3rd stage (total) | 5.0 | 13.0 | 1.77 | 100 | 155 | 2 + 1 = 3 | 10.21 |
| 5 | 1 stage | | 6.42 | 11.77 | 1.60 | 100 | 155 | 1 | 8.92 |
| 6 | 3 stage | 1st stage | 3.0 | 7.0 | 0.95 | 50 | 155 | 1 | 7.32 |
| | | 2nd stage (total) | 4.77 | 9.48 | 1.33 | 75 | 155 | 1 + 1 = 2 | 9.58 |
| | | 3rd stage (total) | 6.42 | 11.77 | 1.60 | 100 | 155 | 2 + 1 = 3 | 11.48 |

The same amount of reactants were used in the examples of each of the compared pairs, i.e., Examples 1 and 2, 3 and 4 and 5 and 6. In Examples 1, 3 and 5, the one stage reaction employed produced lower amounts of ethylene glycol than the corresponding examples employing multistage reactions with which they are compared, i.e., Examples 2, 4 and 6. An increase in the ethylene glycol produced by the one stage reaction is not achieved by conducting the reaction for more than one hour up to three hours as was carried out in the multistage reaction.

EXAMPLES 7-21

Charges of various feed compositions comprising methanol (MeOH), di-tertiary-butyl peroxide (DtBP), formaldehyde (CH₂O) as a mixture of 55 weight percent formaldehyde, 35 weight percent methanol and 10 weight percent water, and a basic material were added to a 304 stainless steel Hoke bomb reactor. The total water in the reaction product did not exceed 5 weight percent of the total reaction product. The reaction temperature was maintained at 155° C. In those examples wherein the reactants were incrementally added to the methanol in two stages, the second portion of each reactant was added to the initial charge one hour after the initial charge was added. In those examples wherein reactants were incrementally added in three stages, the foregoing procedure was followed with the first two stages and a third portion of each reactant was added one hour after the addition of the second portion of the reactant. An hour after the last portion of the reactants was added, the reaction was considered complete and the reactor was cooled by quenching, vented, discharged and the contents analyzed by gas chromatography for ethylene glycol and other products.

The results of these examples are shown in Table II which sets out the total amounts of peroxide, formaldehyde and basic material charged to the reactor containing methanol in the first, second and third stages. The various basic materials used were sodium bicarbonate (NaHCO₃), sodium formate (NaFo), and sodium acetone (NaOAc). The amounts of the reactants used are reported as weight percent of the total material in the reactor up to that stage. The amounts of ethylene glycol are reported as weight percent of the total product mixture.

TABLE II

INCREMENTAL ADDITION OF DI-T-BUTYL PEROXIDE, FORMALDEHYDE AND BASIC MATERIAL TO METHANOL TO PRODUCE ETHYLENE GLYCOL

| Example | Di-t-Butyl Peroxide wt % | | | Formaldehyde wt % | | | Basic Material wt % | | | Basic Material | Wt % EG |
|---|---|---|---|---|---|---|---|---|---|---|---|
| | Stage 1 | Stage 2 | Stage 3 | Stage 1 | Stage 2 | Stage 3 | Stage 1 | Stage 2 | Stage 3 | | |
| 7 | 6.0[1] | 0 | 0 | 6.0[2] | 2.0 | 2.0 | .015 | 0 | 0 | NaHCO₃ | 8.4 |
| 8 | 6.0[1] | 0 | 0 | 6.0[2] | 2.0 | 2.0 | .015 | 0 | .015[3] | NaHCO₃ | 8.3 |
| 9 | 2.0 | 2.0 | 2.0 | 6.0 | 2.0 | 2.0 | .030 | .030 | .030 | NaHCO₃ | 9.7 |
| 10 | 2.0 | 2.0 | 2.0 | 6.0 | 2.0 | 2.0 | .015 | 0 | 0 | NaHCO₃ | 9.2 |
| 11 | 2.0 | 2.0 | 2.0 | 6.0 | 2.0 | 2.0 | .015 | 0 | 0 | NaHCO₃ | 8.7 |
| 12 | 2.0 | 2.0 | 2.0 | 6.0 | 2.0 | 2.0 | .015 | .015 | .015 | NaHCO₃ | 9.2 |
| 13 | 2.0 | 2.0 | 2.0 | 6.0 | 2.0 | 2.0 | .015 | .015 | .015 | NaHCO₃ | 9.3 |
| 14 | 2.0 | 2.0 | 2.0 | 6.0 | 2.0 | 2.0 | .015 | .015 | .015 | NaHCO₃ | 9.6 |
| 15 | 2.0 | 2.0 | 2.0 | 6.0 | 2.0 | 2.0 | .015 | .015 | .015 | NaHCO₃ | 8.7 |
| 16 | 2.0 | 2.0 | 2.0 | 6.0 | 2.0 | 2.0 | .015 | .015 | .015 | NaOAc | 8.9 |
| 17 | 2.0 | 2.0 | 2.0 | 6.0 | 2.0 | 2.0 | .015 | .015 | .015 | NaFo | 8.9 |
| 18 | 2.0 | 2.0 | 2.0 | 6.0 | 2.0 | 2.0 | .015 | .015 | .015 | NaOAc | 9.1 |
| 19 | 2.0 | 2.0 | 2.0 | 6.0 | 2.0 | 2.0 | .015 | .015 | .015 | NaFo | 9.2 |
| 20 | 2.0 | 2.0 | 2.0 | 6.0 | 2.0 | 2.0 | .015 | .015 | .015 | NaOAc | 10.1 |
| 21 | 2.0 | 2.0 | 2.0 | 6.0 | 2.0 | 2.0 | .015 | .015 | .015 | NaOAc | 9.3 |

[1] Total 1 hour reaction period
[2] CH₂O added into second stage after 12 minutes of the reaction and into the third stage after 30 minutes of the reaction
[3] Basic material was added after 30 minutes of the third stage addition for the peroxide and formaldehyde In Examples 7 and 8 the di-tertiary-butyl peroxide was not incrementally added to the methanol. All of the peroxide was present at the beginning of the reaction while the formaldehyde was incrementally added over the reaction period in the presence of sodium bicarbonate to produce 8.3 to 8.4 weight percent ethylene glycol. Higher amounts of ethylene glycol were obtained in Examples 9 through 15 wherein the peroxide and formaldehyde were incrementally added over the reaction period as compared to Examples 7 and 8. The remaining Examples 16 through 21 differ from Examples 9 through 15 in the use of sodium acetate and sodium formate as the basic material instead of sodium bicarbonate. The amounts of ethylene glycol produced in Examples 16 through 21 were generally comparable to the amounts produced in Examples 9 to 15.

reactor up to that stage. The amounts of ethylene glycol are reported as weight percent of the total product mixture.

TABLE III

INCREMENTAL ADDITION OF DI-TERTIARY-BUTYL PEROXIDE, FORMALDEHYDE AND BASIC MATERIAL TO METHANOL TO PRODUCE ETHYLENE GLYCOL

| Example | Di-t-Butyl Peroxide Wt % | | | Formaldehyde Wt % | | | Basic Material Wt % | | | Basic Material | EG Wt % |
|---|---|---|---|---|---|---|---|---|---|---|---|
| | Stage 1 | Stage 2 | Stage 3 | Stage 1 | Stage 2 | Stage 3 | Stage 1 | Stage 2 | Stage 3 | | |
| 22 | 6 | 0 | 0 | 6 | 3 | 3 | .015 | .015 | .015 | NaHCO$_3$ | 8.3 |
| 23 | 6 | 0 | 0 | 6 | 3 | 3 | .015 | 0 | 0 | NaHCO$_3$ | 8.4 |
| 24 | 2 | 2 | 2 | 6 | 3 | 3 | .015 | .015 | .015 | NaHCO$_3$ | 9.8 |
| 25[1] | 2 | 2 | 2 | 6 | 4 | 4 | .015 | .015 | .015 | NaHCO$_3$ | 10.8 |
| 26[2] | 1 + 1 | 1 + 1 | 1 + 1 | 6 + 1.5 | 1.5 + 1.5 | 1.5 + 1.5 | .015 + .015 | .015 + .015 | .015 + .015 | NaHCO$_3$ | 10.2 |
| 27 (1 stage only) | 2 | — | — | 6 | — | — | .015 | — | — | NaHCO$_3$ | 5.4 |
| 28 (2 stages only) | 2 | 2 | — | 6 | 3 | — | .015 | .015 | — | NaHCO$_3$ | 8.0 |
| 29 | 2 | 2 | 2 | 6 | 3 | 3 | .015 | .015 | .015 | NaHCO$_3$ | 8.7 |
| 30 (1 stage only) | 2 | — | — | 6 | — | — | .015 | — | — | NaHCO$_3$ | 5.2 |
| 31 (2 stages only) | 2 | 2 | — | 6 | 3 | — | .015 | .015 | — | NaHCO$_3$ | 8.2 |
| 32 | 2 | 2 | 2 | 6 | 3 | 3 | .015 | .015 | .015 | NaHCO$_3$ | 9.7* |
| | | | | | | | | | | | 9.6 |
| | | | | | | | | | | | 9.5 |
| | | | | | | | | | | | 8.9 |
| 33 (1 stage only) | 2 | — | — | 6 | — | — | .015 | — | — | NaOAc | 6.0 |
| 34 (2 stages only) | 2 | 2 | — | 6 | 3 | — | .015 | .015 | — | NaOAc | 8.5 |
| 35 | 2 | 2 | 2 | 6 | 3 | 3 | .015 | .015 | .015 | NaOAc | 10.1* |
| | | | | | | | | | | | 10.1 |
| | | | | | | | | | | | 9.1 |
| | | | | | | | | | | | 9.1 |
| 36 (1 stage only) | 2 | — | — | 6 | — | — | .015 | — | — | NaFo | 6.1 |
| 37 (2 stages only) | 2 | 2 | — | 6 | 3 | — | .015 | .015 | — | NaFo | 8.3 |
| 38 | 2 | 2 | 2 | 6 | 3 | 3 | .015 | .015 | .015 | NaFo | 9.3* |
| | | | | | | | | | | | 9.2 |
| | | | | | | | | | | | 9.3 |
| | | | | | | | | | | | 8.9 |
| 39 | 2 | 2 | 2 | 6 | 0 | 0 | .015 | 0 | 0 | NaHCO$_3$ | 8.2 |
| 40 (1 stage only) | 4 | 0 | 0 | 8 | 0 | 0 | .015 | 0 | 0 | NaHCO$_3$ | 7.2 |
| 41 (2 stages only) | 2 | 2 | — | 6 | 3 | — | .015 | .015 | — | NaHCO$_3$ | 8.2 |
| 41[2] (2 stages only) | 2 | 2 | — | 6 | 3 | — | .015 | .015 | — | NaHCO$_3$ | 8.6 |

[1]Light ends boiling below point of methanol are removed before the next reactant addition. Light ends include acetone, methanol and methyl formate.
[2]After the initial reactants were charged and reacted for 30 minutes, addition reactants were added at 30 minute intervals.
*Repeat runs under identical conditions.

EXAMPLES 22-42

Charges of various feed compositions comprising methanol (MeOH), di-tertiary-butyl peroxide (DtBP), formaldehyde (CH$_2$O) as a mixture of 55 weight percent formaldehyde, 35 weight percent methanol and 10 weight percent water, and a basic material were added to a 304 stainless steel Hoke bomb reactor. The total water in the reaction product did not exceed 5 weight percent of the total reaction product. The reaction temperature was maintained at 155° C. In those examples wherein the reactants were incrementally added to the methanol in two stages, the second portion of each reactant was added to the initial charge one hour after the initial charge was added. In those examples wherein reactants were incrementally added in three stages, the foregoing procedure was followed with the first two stages and a third portion of each reactant was added one hour after the addition of the second portion of the reactant. An hour after the last portion of the reactants was added, the reaction was considered complete and the reactor was cooled by quenching, vented, discharged and the contents analyzed by gas chromatography for ethylene glycol and other products.

The results of these examples are shown in Table III which sets out the amounts of peroxide, formaldehyde and basic material charged to the reactor containing methanol in the first, second and third stages. The various basic materials used were sodium bicarbonate (NaHCO$_3$), sodium formate (NaFo), and sodium acetate (NaOAc). The amounts of the reactants used are reported as weight percent of the total material in the reactor up to that stage.

Examples 22 and 23 did not employ incremental addition of the di-tertiary-butyl peroxide to the methanol and Example 23 also did not employ incremental addition of the basic material, i.e. sodium bicarbonate. In these examples, all of the peroxide was present at the beginning of the reaction while the formaldehyde was incrementally added over the reaction period. In Examples 24 and 32 illustrating the use of incremental addition of peroxide and formaldehyde, higher amounts of ethylene glycol are obtained as compared to Examples 22 and 23 in which the peroxide is not incrementally added. Example 26 illustrates a six stage addition of the reactants of peroxide, formaldehyde and sodium bicarbonate. Examples 27-29, 30-32, 33-35 and 36-38 each represent a series of results of each stage in a three stage reaction. Example 39 illustrates the incremental addition of peroxide but without the incremental addition of the formaldehyde while Example 40 illustrates a reaction without incremental addition of any type. Example 39 which did not employ incremental addition of formaldehyde, yielded a result in terms of percentage of glycol in the product stream, i.e. 8.2 weight percent, the same as that obtained in Example 41, which employed incremental addition of both peroxide and formaldehyde in two stages. However, these examples are not strictly comparable since Example 39 employed a larger total amount of peroxide while Example 41 employed a larger total amount of formaldehyde.

What is claimed is:

1. In a process for producing ethylene glycol by reacting methanol, formaldehyde and an organic peroxide having the formula R-O-O-R$^1$, wherein each R and R$^1$ is an alkyl or aralkyl group containing from 3 to 12 carbon atoms in a liquid reaction medium, the improvement comprising reacting portions of the total amount of the formaldehyde and peroxide with the methanol in the presence of a basic material present in the reaction medium in an amount sufficient to reduce the hydrogen ions that are formed in the reaction without unduly reducing the ethylene glycol production due to by-product formation, by incrementally adding each of said portions to the reaction medium containing methanol to permit a fraction of the final conversion of said formaldehyde and peroxide to take place prior to the addition of the next added portion, said next added portion being added to said reaction medium wherein said fraction of the final conversion has taken place and containing a concentration of ethylene glycol greater than that of the reaction medium to which said previous portions were added, and continuing the incremental additions until all of said peroxide and formaldehyde has been added to said reaction medium and subjected to reaction to produce the desired amount of ethylene glycol.

2. The process of claim 1 wherein the peroxide is di-tertiarybutyl peroxide.

3. The process of claim 2 wherein the portions of the total amount of the reactants, formaldehyde and di-tertiary-butyl peroxide are added in 2 to 10 stages to the reaction medium containing methanol.

4. The process of claim 3 wherein the peroxide is employed in an amount of about 0.25 to about 25 weight percent, water in amount from about 2 to about 10 weight percent and the formaldehyde in an amount of about 0.5 to about 13 weight of the reaction mixture.

5. The process of claim 2 wherein at least one half of formaldehyde and di-tertiary-butyl peroxide to be reacted is initially reacted in the methanol reaction medium and the remaining portions of formaldehyde and di-tertiary-butyl peroxide are subsequently added.

6. The process of claim 4 wherein a basic material is incrementally added to reaction medium in an amount sufficient to reduce the hydrogen ions that are being formed in the reaction without unduly reducing the ethylene glycol production due to by-product formation.

7. The process of claim 4 wherein the basic material is selected from the group consisting of alkaline earth metal and alkali metal hydroxides; and salts of said metal hydroxides and weakly ionized acids.

8. The process of claim 6 wherein the basic material is selected from the group consisting of alkaline earth and alkali metal hydroxides; and salts of said metal hydroxides and weakly ionized acids.

9. The process of claim 4 wherein the basic material is selected from the group consisting of sodium and potassium hydroxides, acetates, formates, oxalates, carbonates and phosphates.

10. The process of claim 6 wherein the basic material is selected from the group consisting of sodium and potassium hydroxides, acetates, formates, oxalates, carbonates and phosphates.

11. The process of claim 4 wherein the basic material is selected from the group consisting of sodium acetate, potassium acetate, sodium bicarbonate, potassium bicarbonate, sodium formate, potassium formate, sodium oxalate, potassium oxalate, sodium phosphate, potassium phosphate, sodium pyrophosphate and potassium pyrophosphate, said basic material being present in amounts ranging from about 50 to about 3500 parts per million based on the total reaction mixture.

12. The process of claim 6 wherein the basic material is selected from the group consisting of sodium acetate, potassium acetate, sodium bicarbonate, potassium bicarbonate, sodium formate, potassium formate, sodium oxalate, potassium oxalate, sodium phosphate, potassium phosphate, sodium pyrophosphate and potassium pyrophosphate, said basic material being present in amounts ranging from about 50 to about 3500 parts per million based on the total reaction mixture.

13. The process of claim 11 wherein the amount of basic material ranges from about 100 to about 3000 parts per million based on the total reaction mixture.

14. The process of claim 12 wherein the amount of basic material ranges from about 100 to about 3000 parts per million based on the total reaction mixture.

* * * * *